US006989857B2

(12) United States Patent  
Furnas

(10) Patent No.: US 6,989,857 B2  
(45) Date of Patent: Jan. 24, 2006

(54) CONTAINER INSPECTION MACHINE

(75) Inventor: William J. Furnas, Elmira, NY (US)

(73) Assignee: Emhart Glass S.A., Cham (CH)

( * ) Notice: Subject to any disclaimer, the term of this patent is extended or adjusted under 35 U.S.C. 154(b) by 421 days.

(21) Appl. No.: 10/610,417

(22) Filed: Jun. 30, 2003

(65) Prior Publication Data

US 2004/0263618 A1    Dec. 30, 2004

(51) Int. Cl.  
*H04N 7/18*    (2006.01)

(52) U.S. Cl. .................. 348/127; 348/133; 348/143; 348/207; 356/239.1; 356/239.4; 356/239.6; 250/223 B; 250/225

(58) Field of Classification Search ............... 348/127, 348/133, 143, 207; 356/239.1, 239.4, 239.6; 250/223 B, 225  
See application file for complete search history.

(56) References Cited

U.S. PATENT DOCUMENTS

| | | | | |
|---|---|---|---|---|
| 4,002,823 A | * | 1/1977 | Van Oosterhout | ........... 348/127 |
| 5,444,237 A | * | 8/1995 | Takizawa | ................ 250/223 B |
| 6,239,869 B1 | * | 5/2001 | Heuft et al. | ............. 356/239.5 |

* cited by examiner

*Primary Examiner*—Shawn S. An  
(74) *Attorney, Agent, or Firm*—Spencer T. Smith

(57) ABSTRACT

An inspection system completes two inspections with a single camera. In one inspection polarized light illuminates the side wall of a bottle, passes through a pair of electrode surfaces on either side of a ferroelectric crystal which do not change the polarity and passes through a polarizer to image on the camera. In a second inspection the polarized light is rotated 90° by the same structure so that only light rotated as a result of stress in the bottle passes through the polarizer and images on the camera as a defect.

2 Claims, 1 Drawing Sheet

CONTAINER INSPECTION MACHINE

The present invention relates to machines which have a camera based inspection system for inspecting bottles for defects.

BACKGROUND OF THE INVENTION

Machines for inspecting glass bottles conduct a great variety of inspections. More and more of these inspections are conducted using camera technology and each camera adds substantial cost to the system.

OBJECT OF THE INVENTION

It is an object of the present invention to provide a system for inspecting glass containers which will enable a single camera to carry out two inspections.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE PREFERRED EMBODIMENT

Figure 1:
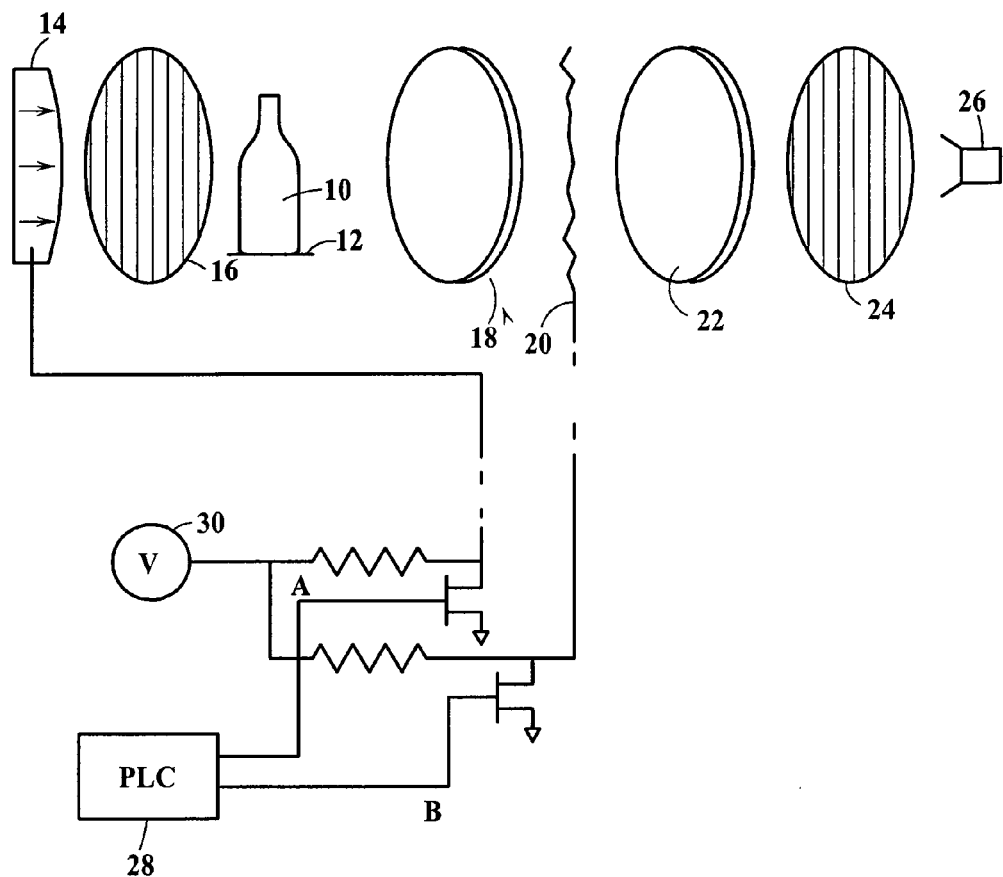
FIG. 1 is a schematic illustration of an inspection machine made in accordance with the teachings of the present invention.

FIG. 1 shows a bottle 10 being conveyed through an inspection station of an inspection machine by a conveyor 12. At a first polarizer 16 and this polarized light this inspection station, a source of light 14 passes through passes through the bottle in a direction perpendicular to the axis of the bottle. The light then passes through a first electrode surface 18, a FLC 20 (ferroelectric liquid crystal), a second electrode surface 22, a second polarizer 24 which has the same polarity as the first polarizer 16, and images on the imaging surface of the camera 26.

The operation of the electrode surfaces is controlled by outputs from a PLC 28 which activate either A or B to apply voltage V 30 to either the first or second electrode surfaces. When A is activated the camera will illuminated with bright polarized light (the electrode surfaces and the FLC define the same polarity as the first and second polarizers) so that the side wall of the bottle can be inspected and when B is activated the camera image will be black (the electrode surfaces and the FLC define a 90° rotated polarity) and as a result light will be blocked except where stress in the bottle due to a defect will change the polarity of the light so that a portion of the light passes through the second polarizer and strikes the camera image indicating a defect.

Figure 2:
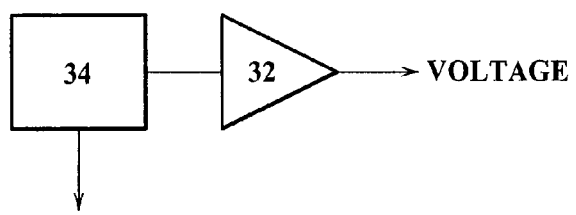
FIG. 2 is a schematic diagram for a temperature correction circuit for the voltage applied in FIG. 1.

FIG. 2 illustrates a temperature correction circuit for adjusting the relative polarization of the system due to environmental temperature variations. Plants were this equipment will be used often have a range of environmental temperatures that can exceed 50° F. It has been found that the contrast ratio of the system (the ratio of light mode to dark mode) is a function of temperature. To correct the error that results from these variations, an amplifier 32 is used which receives a temperature input from a temperature sensor 34 and which will output a voltage that changes over temperature in a way that will maintain the contrast ratio as high as possible over the operating temperature range. This can be effected in software or hardware.

What is claimed is:

1. A machine for inspecting a bottle comprising
   a conveyor for supporting a bottle at an inspection location,
   an inspection system for inspecting a bottle at the inspection location including
      a camera having an imaging surface on one side of the bottle,
      a light source on the other side of the bottle directing light towards said camera,
      a first polarizer between said light source and the bottle, and
      a first electrode surface on the one side of the bottle between the bottle and said camera,
      a ferroelectric liquid crystal on the one side of the bottle between the first electrode and said camera,
      a second electrode surface on the one side of the bottle between the ferroelectric liquid crystal and said camera,
      a second polarizer between said second electrode surface and said camera, and
      controller means for alternately operating said first and second electrode surfaces.

2. A machine for inspecting a bottle according to claim 1, further comprising means for relative rotation of polarized light by said first and second electrodes and said ferroelectric liquid crystal as a function of temperature.

* * * * *